United States Patent [19]

Wideman et al.

[11] Patent Number: 5,753,732
[45] Date of Patent: May 19, 1998

[54] UNSATURATED AMINE-FUNCTIONAL SILANE COMPOUNDS AND THEIR USE IN RUBBER COMPOSITIONS

[75] Inventors: Lawson Gibson Wideman, Tallmadge; David John Zanzig, Uniontown; Theodore Augustus Evans, Canton; Charlie Sun, Hudson, all of Ohio

[73] Assignee: The Goodyear Tire & Rubber Company, Akron, Ohio

[21] Appl. No.: 813,014

[22] Filed: Mar. 6, 1997

[51] Int. Cl.$^6$ .............................. C08F 8/33; C08F 36/06; C07F 7/04
[52] U.S. Cl. .................. 524/263; 525/288; 525/332.6; 556/465; 556/482
[58] Field of Search .......................... 525/288, 332.6; 524/263; 556/465, 482

[56] References Cited

FOREIGN PATENT DOCUMENTS 105078  7/1981  Japan .

Primary Examiner—Irina S. Zemel

Attorney, Agent, or Firm—Bruce J. Hendricks

[57] ABSTRACT

The present invention relates to unsaturated amine-functional silane compounds of the formula:

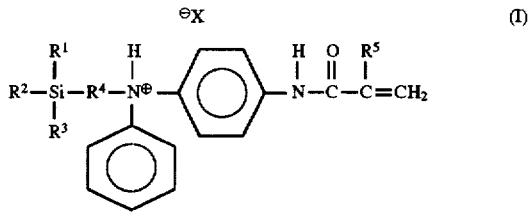

wherein $R^1$, $R^2$ and $R^3$ are independently selected from the group consisting of alkoxy radicals having from 1 to 8 carbon atoms, alkyl radicals having 1 to 8 carbon atoms and aryl radicals having 6 carbon atoms, with the proviso that at least one of $R^1$, $R^2$ and $R^3$ is an alkoxy radical; $R^4$ is selected from the group consisting of alkylene groups having from 1 to 18 carbon atoms and arylene and alkyl substituted arylene groups having from 6 to 10 carbon atoms; $R^5$ is selected from the group consisting of hydrogen and an alkyl group having 1 carbon atom and X is a halogen atom selected from the group consisting of Cl, Br and I.

13 Claims, No Drawings

UNSATURATED AMINE-FUNCTIONAL SILANE COMPOUNDS AND THEIR USE IN RUBBER COMPOSITIONS

FIELD OF THE INVENTION

The present invention relates to unsaturated amine-functional silane compounds and their use in rubber compositions. One example of a rubber article containing the present invention is a rubber tire which has a silica-reinforced rubber tread having a relatively high electrical resistivity such as, for example, a tread cap.

The present invention also relates to a pneumatic tire having a rubber tread containing the unsaturated amine-functional silane compound of the present invention.

BACKGROUND OF THE INVENTION

Pneumatic rubber tires can be prepared with a rubber tread composed of diene-based, sulfur-curable, elastomer(s) which can be quantitatively reinforced with silica and a minimal amount of carbon black, if any. The tire tread is designed to be ground-contacting and is usually of a lug and groove or a rib and groove design. Such designs are well known to those skilled in such art.

The tire may also be of a cap/base construction in which the tread cap is the outer portion of the tread designed to be ground-contacting with the associated lugs and grooves and/or ribs and grooves and the tread base underlies the tread cap and is positioned between the tread cap and the supporting tire carcass. Such tire construction is well known to those skilled in such art.

Rubber by itself, without added ingredients, is generally considered as being substantially an electrical insulator or, in other words, a rather poor conductor of electricity.

A carbon black reinforced rubber vehicular tire, while still providing a degree of resistance to flow of electricity, has a considerably higher electrical conductivity, or lower resistance to flow of electricity, than rubber without the carbon black reinforcement.

Silica is, basically, a relatively poor conductor of electricity and thus a substantially silica-reinforced rubber tire tread which contains only a minimal amount, if any, of carbon black reinforcement is believed to be a relatively good electrical insulator, particularly as compared to a quantitatively carbon black reinforced rubber tire tread.

Sulfur-containing organosilicon compounds are useful as reactive coupling agents between rubber and silica fillers providing for improved physical properties. They are also useful as adhesion primers for glass, metals and other substrates.

U.S. Pat. Nos. 3,842,111, 3,873,489 and 3,978,103 disclose the preparation of various sulfur-containing organosilicon compounds. These organosilicon compounds are commonly used in silica-reinforced rubber.

U.S. Pat. No. 3,734,763 relates to cationic unsaturated amine-functional silane coupling agents. These agents are disclosed for use as a sizing on glass fibers to minimize the build-up of static charge on the fibers.

SUMMARY OF THE INVENTION

The present invention relates to unsaturated amine-functional silane compounds and their use in a rubber.

DETAILED DESCRIPTION OF THE INVENTION

There is disclosed an organosilicon compound comprising an unsaturated amine-functional silane compound of the formula:

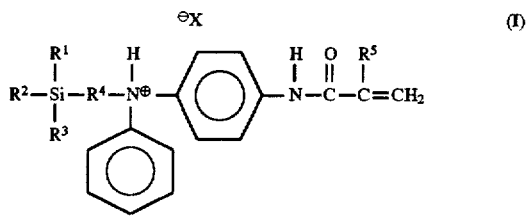

wherein $R^1_1$, $R^2$ and $R^3$ are independently selected from the group consisting of alkoxy radicals having from 1 to 8 carbon atoms, alkyl radicals having 1 to 8 carbon atoms and aryl radicals having 6 carbon atoms, with the proviso that at least one of $R^1$, $R^2$ and $R^3$ is an alkoxy radical; R4 is selected from the group consisting of alkylene groups having from 1 to 18 carbon atoms and arylene and alkyl-substituted arylene groups having from 6 to 10 carbon atoms; and $R^5$ is selected from the group consisting of hydrogen and an alkyl group having 1 carbon atom and X is a halogen selected from the group consisting of Cl, Br and I.

There is disclosed a rubber composition which comprises
(i) 100 parts by weight of at least one sulfur-vulcanizable elastomer containing olefinic unsaturation selected from conjugated diene homopolymers and copolymers and from copolymers of at least one conjugated diene and aromatic vinyl compound;
(ii) 0.05 to 30 phr of an unsaturated amine-functional silane coupling agent of the formula

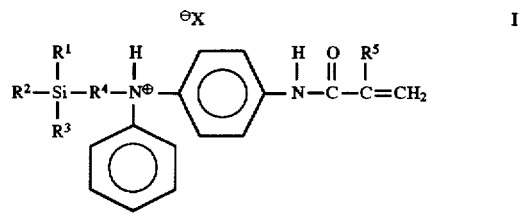

wherein $R^1$, $R^2$ and $R^3$ are independently selected from the group consisting of alkoxy radicals having from 1 to 8 carbon atoms, alkyl radicals having 1 to 8 carbon atoms and aryl radicals having 6 carbon atoms, with the proviso that at least one of $R^1$, $R^2$ and $R^3$ is an alkoxy radical; $R^4$ is selected from the group consisting of alkylene groups having from 1 to 18 carbon atoms and arylene and alkyl-substituted arylene groups having from 6 to 10 carbon atoms; $R^5$ is selected from the group consisting of hydrogen and alkyl group having 1 carbon atom; and x is a halogen selected from the group consisting of Cl, Br and I.

The present invention may be used with sulfur-vulcanizable rubbers or elastomers containing olefinic unsaturation. The phrase "rubber or elastomer-containing olefinic unsaturation" is intended to include both natural rubber and its various raw and reclaim forms as well as various synthetic rubbers. In the description of this invention, the terms "rubber" and "elastomer" may be used interchangeably, unless otherwise prescribed. The terms "rubber composition," "compounded rubber" and "rubber compound" are used interchangeably to refer to rubber which has been blended or mixed with various ingredients and materials and such terms are well known to those having skill in the rubber mixing or rubber compounding art.

Representative synthetic polymers are the homopolymerization products of butadiene and its homologues and derivatives, for example, methylbutadiene, dimethylbutadiene and pentadiene as well as copolymers such as those formed from butadiene or its homologues or derivatives with other unsaturated monomers. Among the latter are acetylenes, for example, vinyl acetylene; olefins, for example, isobutylene, which copolymerizes with isoprene to form butyl rubber; vinyl compounds, for example, acrylic acid, acrylonitrile (which polymerizes with butadiene to form NBR), methacrylic acid and styrene, the latter compound polymerizing with butadiene to form SBR, as well as vinyl esters and various unsaturated aldehydes, ketones and ethers; e.g., acrolein, methyl isopropenyl ketone and vinylethyl ether. Specific examples of synthetic rubbers include neoprene (polychloroprene), polybutadiene (including cis-1,4-polybutadiene), polyisoprene (including cis-1,4-polyisoprene), butyl rubber, styrene/isoprene/butadiene rubber, isoprene-butadiene copolymer, copolymers of 1,3-butadiene or isoprene with monomers such as styrene, acrylonitrile and methyl methacrylate, as well as ethylene/ propylene terpolymers, also known as ethylene/propylene/ diene monomer (EPDM), and in particular, ethylene/ propylene/dicyclopentadiene terpolymers and mixtures of the above. The preferred rubber or elastomers are polybutadiene and SBR.

In one aspect the rubber is at least two diene-based rubbers. For example, a combination of two or more rubbers is preferred such as cis 1,4-polyisoprene rubber (natural or synthetic, although natural is preferred), 3,4-polyisoprene rubber, styrene/isoprene/butadiene rubber, emulsion and solution polymerization derived styrene/butadiene rubbers, cis 1,4-polybutadiene rubbers and emulsion polymerization prepared butadiene/acrylonitrile copolymers.

In one aspect of this invention, an emulsion polymerization derived styrene/butadiene (E-SBR) might be used having a relatively conventional styrene content of about 20 to about 28 percent bound styrene or, for some applications, an E-SBR having a medium to relatively high bound styrene content; namely, a bound styrene content of about 30 to about 45 percent.

The relatively high styrene content of about 30 to about 45 for the E-SBR can be considered beneficial for a purpose of enhancing traction, or skid resistance, of the tire tread. The presence of the E-SBR itself is considered beneficial for a purpose of enhancing processability of the uncured elastomer composition mixture, especially in comparison to a utilization of a solution polymerization prepared SBR (S-SBR).

By emulsion polymerization prepared E-SBR, it is meant that styrene and 1,3-butadiene are copolymerized as an aqueous emulsion. Such are well known to those skilled in such art. The bound styrene content can vary, for example, from about 5 to about 50 percent. In one aspect, the E-SBR may also contain acrylonitrile to form a terpolymer rubber, as E-SBAR, in amounts, for example, of about 2 to about 30 weight percent bound acrylonitrile in the terpolymer.

Emulsion polymerization prepared styrene/butadiene/ acrylonitrile terpolymer rubbers containing about 2 to about 40 weight percent bound acrylonitrile in the terpolymer are also contemplated as diene-based rubbers for use in this invention.

The solution polymerization prepared SBR (S-SBR) typically has a bound styrene content in a range of about 5 to about 50, preferably about 9 to about 36, percent. The S-SBR can be conveniently prepared, for example, by organo lithium catalyzation in the presence of an organic hydrocarbon solvent.

A purpose of using S-SBR is for improved tire rolling resistance as a result of lower hysteresis when it is used in a tire tread composition.

The 3,4-polyisoprene rubber (3,4-PI) is considered beneficial for a purpose of enhancing the tire's traction when it is used in a tire tread composition. The 3,4-PI and use thereof is more fully described in U.S. Pat. No. 5,087,668 which is incorporated herein by reference. The Tg refers to the glass transition temperature which can conveniently be determined by a differential scanning calorimeter at a heating rate of 10° C. per minute.

The cis 1,4-polybutadiene rubber (BR) is considered to be beneficial for a purpose of enhancing the tire tread's wear, or treadwear. Such BR can be prepared, for example, by organic solution polymerization of 1,3-butadiene. The BR may be conveniently characterized, for example, by having at least a 90 percent cis 1,4-content.

The cis 1,4-polyisoprene and cis 1,4-polyisoprene natural rubber are well known to those having skill in the rubber art.

The term "phr" as used herein, and according to conventional practice, refers to "parts by weight of a respective material per 100 parts by weight of rubber, or elastomer."

The unsaturated amine-functional silane compounds of the present invention are of the formula

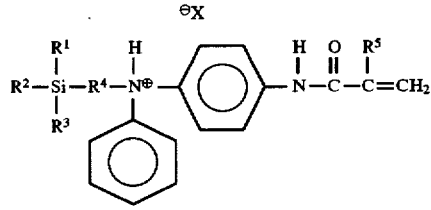

wherein $R^1$, $R^2$ and $R^3$ are independently selected from the group consisting of alkoxy radicals having from 1 to 8 carbon atoms, alkyl radicals having 1 to 8 carbon atoms and aryl radicals having 6 carbon atoms, with the proviso that at least one of $R^1$, $R^2$ and $R^3$ is an alkoxy radical; $R^4$ is selected from the group consisting of alkylene groups having from 1 to 18 carbon atoms and arylene and alkyl substituted arylene groups having from 6 to 10 carbon atoms; $R^5$ is selected from the group consisting of hydrogen and an alkyl group having 1 carbon atom. Preferably, each $R^1$, $R^2$ and $R^3$ are alkoxy radicals having from 1 to 3 carbon atoms, $R^5$ is an alkylene group having from 1 to 3 carbon atoms, $R^5$ is an alkyl group having 1 carbon atom and X is Cl. These amine-functional silane compounds may comprise a high purity product or mixture of amine-functional silane compounds conforming to the above formula I.

Representative of the unsaturated amine-functional silanes of formula I include 4-(methacryloylamino)phenyl-phenyl-3-(trimethoxysilyl) propylamine hydrochloride, 4-(methacryloylamino)phenyl-phenyl-3-(triethoxysilyl) propylamine hydrochloride, 4-(methacryloylamino)phenyl-phenyl-3-(tripropoxysilyl) propylamine hydrochloride, 4-(methacryloylamino)phenyl-phenyl-3-(trimethoxylsilyl) butylamine hydrochloride, 4-(methacryloylamino)phenyl-phenyl-3-(triethoxysilyl) butylamine hydrochloride, 4-(methacryloylamino)phenyl-phenyl-3-(tripropoxysilyl) butylamine hydrochloride, 4-(acryloylamino)phenyl-phenyl-3-(trimethoxysilyl) propylamine hydrochloride, 4-(acryloylamino)phenyl-phenyl-3-(triethoxysilyl) propylamine hydrochloride, 4-(acryloylamino)phenyl-phenyl-3-(tripropoxysilyl) propylamine hydrochloride.
4-(acryloylamino)phenyl-phenyl-3-(trimethoxysilyl) butylamine hydrochloride,
4-(acryloylamino)phenyl-phenyl-3-(triethoxysilyl) butylamine hydrochloride.
4-(acryloylamino)phenyl-phenyl-3-(tripropoxysilyl) butylamine hydrochloride.
4-(methacryloylamino)phenyl-phenyl-3-(trimethoxysilyl) propylamine hydrobromide,
4-(methacryloylamino)phenyl-phenyl-3-(triethoxysilyl) propylamine hydrobromide,
4-(methacryloylamino)phenyl-phenyl-3-(tripropoxysilyl) propylamine hydrobromide.
4-(methacryloylamino)phenyl-phenyl-3-(trimethoxylsilyl) butylamine hydrobromide,
4-(methacryloylamino)phenyl-phenyl-3-(triethoxysilyl) butylamine hydrobromide,
4-(methacryloylamino)phenyl-phenyl-3-(tripropoxysilyl) butylamine hydrobromide.
4-(acryloylamino)phenyl-phenyl-3-(trimethoxysilyl) propylamine hydrobromide,
4-(acryloylamino)phenyl-phenyl-3-(triethoxysilyl) propylamine hydrobromide.
4-(acryloylamino)phenyl-phenyl-3-(tripropoxysilyl) propylamine hydrobromide,
4-(acryloylamino)phenyl-phenyl-3-(trimethoxysilyl) butylamine hydrobromide,
4-(acryloylamino)phenyl-phenyl-3-(triethoxysilyl) butylamine hydrobromide,
4-(acryloylamino)phenyl-phenyl-3-(tripropoxysilyl) butylamine hydrobromide.
4-(methacryloylamino)phenyl-phenyl-3-(trimethoxysilyl) propylamine hydroiodide.
4-(methacryloylamino)phenyl-phenyl-3-(triethoxysilyl) propylamine hydroiodide,
4-(methacryloylamino)phenyl-phenyl-3-(tripropoxysilyl) propylamine hydroiodide,
4-(methacryloylamino)phenyl-phenyl-3-(trimethoxylsilyl) butylamine hydroiodide.
4-(methacryloylamino)phenyl-phenyl-3-(triethoxysilyl) butylamine hydroiodide,
4-(methacryloylamino)phenyl-phenyl-3-(tripropoxysilyl) butylamine hydroiodide.
4-(acryloylamino)phenyl-phenyl-3-(trimethoxysilyl) propylamine hydroiodide.
4-(acryloylamino)phenyl-phenyl-3-(triethoxysilyl) propylamine hydroiodide.
4-(acryloylamino)phenyl-phenyl-3-(tripropoxysilyl) propylamine hydroiodide,
4-(acryloylamino)phenyl-phenyl-3-(trimethoxysilyl) butylamine hydroiodide,
4-(acryloylamino)phenyl-phenyl-3-(triethoxysilyl) butylamine hydroiodide and
4-(acryloylamino)phenyl-phenyl-3-(tripropoxysilyl) butylamine hydroiodide.

The compounds of formula I are prepared by the reaction of a silyl-substituted (alkylene, arylene or alkarylene) halide of the formula

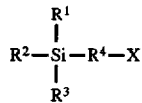

II with a conjugated unsaturated amine of the formula

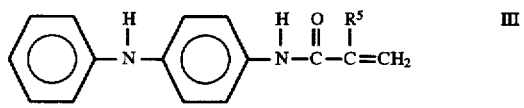

III where $R^1$, $R^2$, $R^3$, $R^4$, $R^5$ and X have been defined above.

The molar ratio of the compound of formula II to the compound of formula III may range from 1:5 to 5:1. Preferably, the molar ratio ranges from 1:3 to 3:1 with a range of from 1:1 being particularly preferred.

The reaction should be conducted in the absence of water because the presence of an alkoxysilane moiety may be hydrolysed by contact with water.

The reaction of the present invention may be conducted in the presence of an organic solvent. Suitable solvents which may be used but are not limited to include chloroform, dichloromethane, carbon tetrachloride, hexane, heptane, cyclohexane, xylene, benzene, dichloroethylene, trichloroethylene, dioxane, diisopropyl ether, tetrahydrofuran, anhydrous tert-butyl alcohol, anhydrous isopropanol, anhydrous ethanol, anhydrous methanol and toluene. As indicated above, care should be exercised to avoid the presence of water during the reaction. Therefore, none of the above solvents should contain any appreciable levels of water. Preferably, the organic solvent is chloroform, heptane, cyclohexane, anhydrous ethanol, xylene and toluene.

The reaction may be conducted over a variety of temperatures. Generally speaking, the reaction is conducted in a temperature ranging from 20° C. to 140° C. Preferably, the reaction is conducted at a temperature ranging from 50° C. to 90° C.

The process of the present invention may be conducted at a variety of pressures. Generally speaking, however, the reaction is conducted at a pressure ranging from 0.096 to 4.83 kg/cm$^2$.

The unsaturated amine-functional silanes of the present invention may be added to the rubber by any conventional technique such as on a mill or in a Banbury. The amount of the unsaturated amine-functional silane may vary widely depending on the type of rubber and other compounds present in the rubber composition. Generally, the amount of the unsaturated amine-functional silane compound is used in a range of from about 0.05 to about 30.0 phr with a range of 0.1 to about 10.0 phr being preferred. The unsaturated amine-functional silane may be added to the rubber during the nonproductive and/or productive mix stage. Preferably, the amine-functional silane compound is added in the nonproductive mix stage with a silica filler.

For ease in handling, the unsaturated amine functional silane may be used per se or may be deposited on suitable carriers. Examples of carriers which may be used in the present invention include but are not limited to silica, carbon black, alumina, alumina silicates, clay, kieselguhr, cellulose, silica gel and calcium silicate.

The rubber composition preferably contains a sufficient amount of silica, and carbon black, if used, to contribute a reasonably high modulus and high resistance to tear. The silica filler may be added in amounts ranging from 10 to 250 phr. Preferably, the silica is present in an amount ranging from 15 to 90 phr. If carbon black is also present, the amount of carbon black, if used, may vary. Generally speaking, the amount of carbon black will vary from 0 to 80 phr. Preferably, the amount of carbon black will range from 10 to 40 phr. It is to be appreciated that the unsaturated amine functional compound may be used in conjunction with a carbon black, namely pre-mixed with a carbon black prior to addition to the rubber composition, and such carbon black is to be included in the aforesaid amount of carbon black for the rubber composition formulation.

The commonly employed siliceous pigments used in conventional rubber compounding applications may be used as the silica in this invention, including pyrogenic and precipitated siliceous pigments (silica) and aluminosilicates, although precipitated silicas are preferred. The siliceous pigments preferably employed in this invention are precipitated silicas such as, for example, those obtained by the acidification of a soluble silicate, e.g., sodium silicate.

Such silicas might be characterized, for example, by having a BET surface area, as measured using nitrogen gas, preferably in the range of about 40 to about 600, and more usually in a range of about 50 to about 300 square meters per gram. The BET method of measuring surface area is described in the *Journal of the American Chemical Society*, Volume 60, page 304 (1930).

The silica may also be typically characterized by having a dibutylphthalate (DBP) absorption value in a range of about 100 to about 400, and more usually about 150 to about 300.

Further, the silica, as well as the aforesaid alumina and aluminosilicate may be expected to have a CTAB surface area in a range of about 100 to about 220. The CTAB surface area is the external surface area as evaluated by cetyl trimethylammonium bromide with a pH of 9. The method is described in ASTM D 3849 for set up and evaluation. The CTAB surface area is a well known means for characterization of silica.

Mercury surface area/porosity is the specific surface area determined by mercury porosimetry. For such technique, mercury is penetrated into the pores of the sample after a thermal treatment to remove volatiles. Set-up conditions may be suitably described as using a 100 mg sample; removing volatiles during 2 hours at 105° C. and ambient atmospheric pressure; ambient to 2000 bars pressure measuring range. Such evaluation may be performed according to the method described in Winslow, Shapiro in ASTM bulletin, p.39 (1959) or according to DIN 66133. For such an evaluation, a CARLO-ERBA Porosimeter 2000 might be used.

The average mercury porosity specific surface area for the silica should be in a range of about 100 to 300 m²/g.

A suitable pore-size distribution for the silica, alumina and aluminosilicate according to such mercury porosity evaluation is considered herein to be 5 percent or less of its pores have a diameter of less than about 10 nm; 60 to 90 percent of its pores have a diameter of about 10 to about 100 nm; 10 to 30 percent of its pores have a diameter of about 100 to about 1000 nm; and 5 to 20 percent of its pores have a diameter of greater than about 1000 nm.

The silica might be expected to have an average ultimate particle size, for example, in the range of 0.01 to 0.05 micron as determined by the electron microscope, although the silica particles may be even smaller, or possibly larger, in size.

Various commercially available silicas may be considered for use in this invention such as, only for example herein, and without limitation, silicas commercially available from PPG Industries under the Hi-Sil trademark with designations 210, 243, etc; silicas available from Rhone-Poulenc, with, for example, designations of Zeosil™ 1165MP and Z165GR and silicas available from Degussa AG with, for example, designations VN2, VN3, BV3380GR, etc, and silicas available from Huber, for example Huber Sil 8745.

The unsaturated amine-functional silane of formula I functions as a rubber processing aid and enhances the anti-static properties of the silica-filled rubber. The unsaturated amine-functional silane may be used in combination with a sulfur-containing organosilicon compounds. Examples of suitable sulfur-containing organosilicon compounds are of the formula:

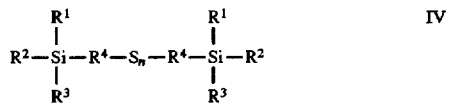

wherein n is an integer of from 2 to 8 and $R^1$, $R^2$, $R^3$ and $R^4$ have been defined above. Preferably, n is an integer of from 2 to 4, $R^1$, $R^2$ and $R^3$ are each an alkoxy radical having 1 to 3 carbon atoms and $R^4$ is an alkylene group having from 1 to 3 carbon atoms.

Specific examples of sulfur-containing organosilicon compounds of formula IV which may be used in accordance with the present invention include: 3,3'-bis (trimethoxysilylpropyl) disulfide, 3,3'-bis (triethoxysilylpropyl) tetrasulfide, 3,3'-bis (triethoxysilylpropyl) octasulfide, 3,3'-bis (trimethoxysilylpropyl) tetrasulfide, 2,2'-bis (triethoxysilylethyl) tetrasulfide, 3,3'-bis (trimethoxysilylpropyl) trisulfide, 3,3'-bis (triethoxysilylpropyl) trisulfide, 3,3'-bis (tributoxysilylpropyl) disulfide, 3,3'-bis (trimethoxysilylpropyl) hexasulfide, 3,3'-bis (trimethoxysilylpropyl) octasulfide, 3,3'-bis (trioctoxysilylpropyl) tetrasulfide, 3,3'-bis (trihexoxysilylpropyl) disulfide, 3,3'-bis(tri-2'-ethylhexoxysilylpropyl) trisulfide, 3,3'-bis (triisooctoxysilylpropyl) tetrasulfide, 3,3'-bis(tri-t-butoxysilylpropyl) disulfide, 2,2'-bis(methoxy diethoxy silyl ethyl) tetrasulfide, 2,2'-bis(tripropoxysilylethyl) pentasulfide, bis(trimethoxysilylmethyl) tetrasulfide, 3-methoxy ethoxy propoxysilyl 3'-diethoxybutoxysilylpropyltetrasulfide, 2,2'-bis(dimethyl methoxysilylethyl) disulfide, 2,2'-bis(dimethyl sec.butoxysilylethyl) trisulfide, 3,3'-bis(methyl butylethoxysilylpropyl) tetrasulfide, 3,3'-bis(di t-butylmethoxysilylpropyl) tetrasulfide, 2,2'-bis(phenyl methyl methoxysilylethyl) trisulfide, 3,3'-bis(diphenyl isopropoxysilylpropyl) tetrasulfide, 3,3'-bis(dimethyl ethylmercaptosilylpropyl) tetrasulfide, 2,2'-bis(methyl dimethoxysilylethyl) trisulfide, 2,2'-bis(methyl ethoxypropoxysilylethyl) tetrasulfide, 3,3'-bis(diethyl methoxysilylpropyl) tetrasulfide, 3,3'-bis(ethyl di-sec. butoxysilylpropyl) disulfide, 3,3'-bis(propyl diethoxysilypropyl) disulfide, 3,3'-bis(butyl dimethoxysilylpropyl) trisulfide, 3,3'-bis(phenyl dimethoxysilylpropyl) tetrasulfide, 3-phenyl ethoxybutoxysilyl 3'-trimethoxysilylpropyl tetrasulfide, 4,4'-bis (trimethoxysilylbutyl) tetrasulfide, 6,6'-bis (triethoxysilylhexyl) tetrasulfide, 12,12'-bis (triisopropoxysilyl dodecyl) disulfide, 18,18'-bis (trimethoxysilyloctadecyl) tetrasulfide, 18,18'-bis (tripropoxysilyloctadecenyl) tetrasulfide, 4,4'-bis (trimethoxysilylcyclohexylene) tetrasulfide, 5,5'-bis (dimethoxymethylsilylpentyl) trisulfide, 3,3'-bis (trimethoxysilyl-2-methylpropyl) tetrasulfide, 3,3-1-bis (dimethoxyphenylsilyl-2-methylpropyl) disulfide.

The preferred sulfur-containing organosilicon compounds of formula IV are the 3,3'-bis(trimethoxy or triethoxy silylpropyl) sulfides. The most preferred compounds are 3,3'-bis(triethoxysilylpropyl) tetrasulfide and 3,3'-bis (triethoxysilylpropyl) disulfide.

The amount of the above sulfur-containing organosilicon compound in a rubber composition will vary depending on the level of silica that may be used. Generally speaking, the amount of the compound of formula IV will range from 0.05 to 10.0 phr. Preferably, the amount will range from 0.1 to 8 phr.

In accordance with one aspect of this invention, a silica-filled rubber composition is prepared by a process which includes the step of thermomechanically mixing in at least one preparatory mixing step to a rubber compound temperature of about 100° C. to about 190° C., for a total mixing time of about 1 to about 20 minutes (i) 100 parts by weight of at least one sulfur-vulcanizable elastomer selected from conjugated diene homopolymers and copolymers and copolymers of at least one conjugated diene and aromatic vinyl compound; (ii) about 10 to about 250 phr of particulate filler selected from the group consisting of precipitated silica; and (iii) about 0.05 to about 30.0 phr of at least one unsaturated amine-functional silane compound of formula I. Preferably, the mixing step involves mixing the rubber compound at a temperature ranging from rubber compound composition of about 155° C. to 175° C. for a duration of from 1 to 7 minutes. Preferably, a sulfur-containing organosilicon compound of formula IV is present.

It is readily understood by those having skill in the art that the rubber composition would be compounded by methods generally known in the rubber compounding art, such as mixing the various sulfur-vulcanizable constituent rubbers with various commonly used additive materials such as, for example, sulfur donors, curing aids, such as activators and retarders and processing additives, such as oils, resins including tackifying resins and plasticizers, fillers, pigments, fatty acid, zinc oxide, waxes, antioxidants and antiozonants and peptizing agents. As known to those skilled in the art, depending on the intended use of the sulfur-vulcanizable and sulfur-vulcanized material (rubbers), the additives mentioned above are selected and commonly used in conventional amounts. Typical amounts of reinforcing-type carbon blacks(s), for this invention, if used, are herein set forth. Representative examples of sulfur donors include elemental sulfur (free sulfur), an amine disulfide, polymeric polysulfide and sulfur olefin adducts. Preferably, the sulfur-vulcanizing agent is elemental sulfur. The sulfur-vulcanizing agent may be used in an amount ranging from 0.5 to 8 phr, with a range of from 1.5 to 6 phr being preferred. Typical amounts of tackifier resins, if used, comprise about 0.5 to about 10 phr, usually about 1 to about 5 phr. Typical amounts of processing aids comprise about 1 to about 50 phr. Such processing aids can include, for example, aromatic, napthenic, and/or paraffinic processing oils. Typical amounts of antioxidants comprise about 1 to about 5 phr. Representative antioxidants may be, for example, diphenyl-p-phenylenediamine and others, such as, for example, those disclosed in the *Vanderbilt Rubber Handbook* (1978), pages 344–346. Typical amounts of antiozonants comprise about 1 to 5 phr. Typical amounts of fatty acids, if used, which can include stearic acid, comprise about 0.5 to about 3 phr. Typical amounts of zinc oxide comprise about 2 to about 5 phr. Typical amounts of waxes comprise about 1 to about 5 phr. Often microcrystalline and paraffinic waxes are used. Typical amounts of peptizers comprise about 0.1 to about 1 phr. Typical peptizers may be, for example, pentachlorothiophenol and dibenzamidodiphenyl disulfide.

In one aspect of the present invention, the sulfur-vulcanizable rubber composition is then sulfur-cured or vulcanized.

Accelerators are used to control the time and/or temperature required for vulcanization and to improve the properties of the vulcanizate. In one embodiment, a single accelerator system may be used; i.e., primary accelerator. The primary accelerator(s) may be used in total amounts ranging from about 0.5 to about 4, preferably about 0.8 to about 2.0, phr. In another embodiment, combinations of a primary and a secondary accelerator might be used with the secondary accelerator being used in a smaller, equal or greater amount to the primary accelerator. Combinations of these accelerators might be expected to produce a synergistic effect on the final properties and are somewhat better than those produced by use of either accelerator alone. In addition, delayed action accelerators may be used which are not affected by normal processing temperatures but produce a satisfactory cure at ordinary vulcanization temperatures. Vulcanization retarders might also be used. Suitable types of accelerators that may be used in the present invention are amines, disulfides, guanidines, thioureas, thiazoles, thiurams, sulfenamides, dithiocarbamates and xanthates. Preferably, the primary accelerator is a sulfenamide. If a second accelerator is used, the secondary accelerator is preferably a guanidine, dithiocarbamate or thiuram compound.

The mixing of the rubber composition can be accomplished by methods known to those having skill in the rubber mixing art. For example, the ingredients are typically mixed in at least two stages, namely at least one non-productive stage followed by a productive mix stage. The final curatives including sulfur-vulcanizing agents are typically mixed in the final stage which is conventionally called the "productive" mix stage in which the mixing typically occurs at a temperature, or ultimate temperature, lower than the mix temperature(s) than the preceding non-productive mix stage (s). The rubber, silica, if used, and the unsaturated amine-functional silane compound of formula I are mixed in one or more non-productive mix stages although the unsaturated amine-functional silane compound may be added to the productive stage. The terms "non-productive" and "productive" mix stages are well known to those having skill in the rubber mixing art. The non-productive sulfur-vulcanizable rubber composition containing the unsaturated amine-functional silane compound of formula I, vulcanizable rubber and generally at least part of the silica, if used, may be subjected to a thermomechanical mixing step. The thermomechanical mixing step generally comprises a mechanical working in a mixer or extruder for an extended period of time at a rubber temperature discussed above.

In further accordance with the invention, the process comprises the additional step of vulcanizing the prepared rubber composition at a temperature in a range of about 100° C. to about 200° C.

Accordingly, the invention also thereby contemplates a vulcanized rubber composition prepared by such process.

In additional accordance with the invention, the process comprises the additional steps of preparing an assembly of a tire or sulfur-vulcanizable rubber with a tread comprised of the said rubber composition prepared according to the process of this invention and vulcanizing the assembly at a temperature in a range of about 100° C. to about 200° C.

Accordingly, the invention also thereby contemplates a vulcanized tire prepared by such process.

Vulcanization of the rubber composition of the present invention is generally carried out at conventional temperatures ranging from about 100° C. to 200° C. Preferably, the vulcanization is conducted at temperatures ranging from about 110° C. to 180° C. Any of the usual vulcanization processes may be used such as heating in a press or mold, heating with superheated steam or hot air or in a salt bath.

Upon vulcanization of the sulfur-vulcanized composition, the rubber composition of this invention can be used for various purposes. For example, the sulfur-vulcanized rubber composition may be in the form of a tire, belt or hose. In case of a tire, it can be used for various tire components. Such tires can be built, shaped, molded and cured by various methods which are known and will be readily apparent to those having skill in such art. Preferably, the rubber composition is used in the tread of a tire. As can be appreciated, the tire may be a passenger tire, aircraft tire, truck tire and the like. Preferably, the tire is a passenger tire. The tire may also be a radial or bias, with a radial tire being preferred.

EXAMPLE 1

Preparation of the Unsaturated Amine-Functional Silane

A 1-liter round-bottom flask was charged with 50.4 g (0.20 mole) of N-(4-methyacryloylamine) diphenylamine, 200 ml of absolute ethanol and 52.0 g (0.22 mole) of 3-chloropropyltriethoxysilane. The reaction system was sealed under nitrogen and heated with stirring to reflux. After 2 hours of reflux, the reaction mixture was cooled to room temperature and the volatiles removed under a reduced pressure of 29 inches of mercury vacuum at 50° C. to give 72.4 g of a light green-colored semi-solid. Infrared Spectroscopic analysis showed disappearance of the secondary amine stretching bands to hydrogen and the secondary amine to hydrogen bending vibration bands shifting to those of an amine salt.

EXAMPLE 2

Preparation of the Unsaturated Amine-Functional Silane

A 1-liter round-bottom flask was charged with 300 ml of absolute methanol, 50.4 g (0.20 mole) of N-(4-methacryloylamino)diphenylamine and 52.0 g (0.22 mole) of 3-chloropropyltriethoxysilane. The reaction mixture was flushed and sealed with nitrogen and stirred as it was heated to reflux for 3 hours, before being cooled to room temperature. The volatiles were removed at 50° C. under a reduced pressure of 29 inches of mercury vacuum to give 75.5 g of a light green-colored semi-solid. Infrared Spectroscopic analysis was the same as found for the product of Example 1.

EXAMPLE 3

Each rubber stock was prepared in a one-stage non-productive and one-stage productive Banbury mix procedure. The recipe for each rubber compound is listed in Table I. All parts and percentages are by weight (parts by weight per 100 parts of rubber "phr") unless otherwise noted.

Cure properties were determined using a Monsanto oscillating disc rheometer which was operated at a temperature of 150° C. or 190° C. and 100 cycles per minute. A description of oscillating disc rheometers can be found in the Vanderbilt Rubber Handbook edited by Robert O. Ohm (Norwalk, Conn., R. T. Vanderbilt Company, Inc., 1990), pages 554–557. The use of this cure meter and standardized values read from the curve are specified in ASTM D-2084. A typical cure curve obtained on an oscillating disc rheometer is shown on page 555 of the 1990 edition of the Vanderbilt Rubber Handbook.

In such an oscillating disc rheometer, compounded rubber samples are subjected to an oscillating shearing action of constant amplitude. The torque of the oscillating disc embedded in the stock that is being tested that is required to oscillate the rotor at the vulcanization temperature is measured. The values obtained using this cure test are very significant since changes in the rubber or the compounding recipe are very readily detected.

G' is a measure of dynamic stiffness at a given percent strain.

Electrical Resistivity was determined according to ASTM D257:D&C Resistance or Conductance of Insulting Materials.

The following Table II reports cure properties that were obtained for the rubber stocks that were prepared. These properties include minutes to 25 percent of the torque increase (t25), minutes to 90 percent of the torque increase (t90), marching modulus and reversion.

TABLE I

|  | Control Sample 1 | Control Sample 2 | Present Invention Sample 3 |
| --- | --- | --- | --- |
| Non-Productive |  |  |  |
| Polybutadiene[1] | 30.0 | 30.0 | 30.0 |
| SBR[2] | 70.0 | 70.0 | 70.0 |
| Zinc Oxide | 3.5 | 3.5 | 3.5 |
| Aromatic Oil | 28.0 | 28.0 | 28.0 |
| Stearic Acid | 2.0 | 2.0 | 2.0 |
| Wax | 3.5 | 3.5 | 3.5 |
| TMQ[3] | 1.0 | 1.0 | 1.0 |
| Antiozonant[4] | 1.0 | 1.0 | 1.0 |
| Silica[5] | 70.0 | 70.0 | 70.0 |
| Carbon Black[6] | 5.5 | 0 | 5.5 |
| Organosilane[7] | 0 | 11.0 | 0 |
| Amine-Silane of Example 1 | 0 | 0 | 5.5 |
| Productive |  |  |  |
| Accelerator[8] | 1.7 | 1.7 | 1.7 |
| Accelerator[9] | 2.0 | 2.0 | 2.0 |
| Sulfur | 1.4 | 1.4 | 1.4 |

[1]Polybutadiene commercially available from The Goodyear Tire & Rubber Company under the designation Budene ® 1207.
[2]Solution polymerized styrene-butadiene rubber commercially available from The Goodyear Tire & Rubber Company under the designation Solflex ® 1216.
[3]Polymerized 1,2-dihydro-2,2,4-trimethylquinoline commercially available from The B F Goodrich Company.
[4]N-1,3-dimethylbutyl N'-phenyl paraphenylene diamine
[5]Zeosil ™ 1165 MP
[6]N330
[7]3,3'-bis(triethoxysilylpropyl)tetrasulfide on carbon black (50 percent by weight carbon black) commercially available from Degussa A G under the designation Si69 ™.
[8]N-cyclohexyl benzothiazole-2-sulfenamide
[9]Diphenyl guanidine

TABLE II

|  | Control Sample 1 | Control Sample 2 | Sample 3 |
| --- | --- | --- | --- |
| Modulus (MPa) 36'/150° C. |  |  |  |
| 100% | 1.35 | 2.14 | 1.19 |
| 300% | 2.51 | 10.04 | 2.35 |
| M300/M100 | 1.86 | 4.69 | 2.00 |
| Tensile Breakstrength (MPa) | 11.17 | 15.47 | 11.03 |
| Elongation @ Break (%) | 970 | 430 | 923 |
| Hardness @ Room Temp | 65.5 | 61.7 | 63.8 |
| Rebound @ Room Temp (%) | 38.9 | 47.7 | 31.1 |
| RPA 11 hz, 100° C. (KPa) |  |  |  |
| G' 1% | 5210 | 2015 | 4035 |
| G' 5% | 3334 | 1687 | 2415 |

TABLE II-continued

|  | Control Sample 1 | Control Sample 2 | Sample 3 |
|---|---|---|---|
| G' 10% | 2210 | 1498 | 1648 |
| G' 14% | 1771 | 1405 | 1360 |
| tan delta, 14% strain | .235 | .103 | .218 |
| Rubber Process Analyzer |  |  |  |
| Uncured G', 100° C., 15%, .83 Hz | 410 | 260 | 260 |
| Volume Resistivity (Ohm* cm) | $1.05 \times 10^{15}$ | $1.81 \times 10^{14}$ | $1.09 \times 10^{14}$ |

As can be seen from the above data, the sample of the present invention has over a 10-fold improvement in a lower volume resistivity (lower is better) and roughly 80 percent improvement versus the use of a conventional sulfur-containing organosilicon.

As to the remaining properties, uncured G' is a measure of compound viscosity. Lower values are preferred for rubber processing. Use of the compounds of the present invention result in lowering the uncured viscosity (Compound 3) in a similar manner to conventional silica coupling agents (Control 2).

The cured G' values at low strain (1%) also indicate desired lower dynamic stiffness values with use of the present invention (Sample 3) versus the same compound without the use of the present invention (Control 1).

While certain representative embodiments and details have been shown for the purpose of illustrating the invention, it will be apparent to those skilled in this art that various changes and modifications may be made therein without departing from the spirit or scope of the invention.

What is claimed is:

1. An organosilicon compound comprising an unsaturated amine-functional silane compound of the formula:

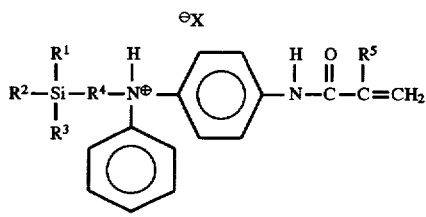

wherein $R^1$, $R^2$ and $R^3$ are independently selected from the group consisting of alkoxy radicals having from 1 to 8 carbon atoms, alkyl radicals having 1 to 8 carbon atoms and aryl radicals having 6 carbon atoms, with the proviso that at least one of $R^1$, $R^2$ and $R^3$ is an alkoxy radical; $R^4$ is selected from the group consisting of alkylene groups having from 1 to 18 carbon atoms and arylene and alkyl-substituted arylene groups having from 6 to 10 carbon atoms; $R^5$ is selected from the group consisting of hydrogen and an alkyl group having 1 carbon atom; and X is a halogen selected from the group consisting of Cl, Br and I.

2. The compound of claim 1 wherein $R^1$, $R^2$ and $R^3$ are each an alkoxy radical having from 1 to 3 carbon atoms, $R^4$ is an alkylene group having from 1 to 3 carbon atoms, $R^5$ is an alkyl group having 1 carbon atom and X is Cl.

3. A rubber composition which comprises
   (i) 100 parts by weight of at least one sulfur-vulcanizable elastomer containing olefinic unsaturation selected from conjugated diene homopolymers and copolymers and from copolymers of at least one conjugated diene and aromatic vinyl compound; and
   (ii) 0.05 to 30 phr of an unsaturated amine-functional silane of the formula:

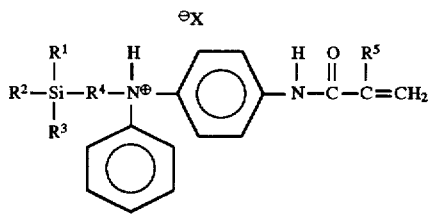

wherein $R^1$, $R^2$ and $R^3$ are independently selected from the group consisting of alkoxy radicals having from 1 to 8 carbon atoms, alkyl radicals having 1 to 8 carbon atoms and aryl radicals having 6 carbon atoms, with the proviso that at least one of $R^1$, $R^2$ and $R^3$ is an alkoxy radical; $R^4$ is selected from the group consisting of alkylene groups having from 1 to 18 carbon atoms and arylene and alkyl-substituted arylene groups having from 6 to 10 carbon atoms; $R^5$ is selected from the group consisting of hydrogen and an alkyl group having 1 carbon atom; and X is a halogen selected from the group consisting of Cl, Br and I.

4. The composition of claim 3 wherein each $R^1$, $R^2$ and $R^3$ are alkoxy radicals having 1 to 3 carbon atoms, $R^4$ is an alkylene group having 1 to 3 carbon atoms, R5 is an alkyl group having 1 carbon atom and X is Cl.

5. The composition of claim 3 wherein particulate precipitated silica is present in an amount ranging from 10 to 250 phr.

6. The composition of claim 3 wherein said elastomer containing olefinic unsaturation is selected from the group consisting of natural rubber, neoprene, polyisoprene, butyl rubber, polybutadiene, styrene-butadiene copolymer, styrene/isoprene/butadiene rubber, methyl methacrylate-butadiene copolymer, isoprene-styrene copolymer, methyl methacrylate-isoprene copolymer, acrylonitrile-isoprene copolymer, acrylonitrile-butadiene copolymer, EPDM and mixtures thereof.

7. The composition of claim 5 wherein a sulfur-containing organosilicon compound of the formula

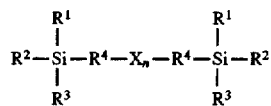

is present, wherein n is an integer of from 2 to 8, $R^1$, $R^2$ and $R^3$ are independently selected from the group consisting of alkoxy radicals having from 1 to 8 carbon atoms, alkyl radicals having 1 to 8 carbon atoms and aryl radicals having 6 carbon atoms, with the proviso that at least one of $R^1$, $R^2$ and $R^3$ is an alkoxy radical; and $R^4$ is selected from the group consisting of alkylene groups having from 1 to 18 carbon atoms and arylene and alkyl-substituted arylene groups having from 6 to 10 carbon atoms.

8. The composition of claim 7 wherein n is an integer of from 2 to 4, $R^1$, $R^2$ and $R^3$ are each an alkoxy radical having 1 to 3 carbon atoms and $R^4$ is an alkylene group having from 1 to 3 carbon atoms.

9. The composition of claim 7 wherein from 0.05 to 10.0 phr of said sulfur-containing organosilicon compound is present.

10. The composition of claim 7 wherein said composition was thermomechanically mixed at a rubber temperature in a range of from 100° C. to 190° C. for a total mixing time of from 1 to 20 minutes.

11. A sulfur-vulcanized rubber composition which is prepared by heating the composition of claim 3 to a temperature ranging from 100° C. to 200° C. in the presence of a sulfur-vulcanizing agent.

12. The sulfur-vulcanized rubber composition of claim 11 in the form of a tire, belt or hose.

13. A tire having a tread comprised of the composition of claim 11.

* * * * *